US012559512B2

(12) United States Patent
Saito et al.

(10) Patent No.: US 12,559,512 B2
(45) Date of Patent: Feb. 24, 2026

(54) METHOD FOR PRODUCING GLYCOSIDE COMPOUND

(71) Applicant: SUMITOMO CHEMICAL COMPANY, LIMITED, Chuo-ku (JP)

(72) Inventors: Tatsuya Saito, Osaka (JP); Hideki Ihara, Osaka (JP)

(73) Assignee: SUMITOMO CHEMICAL COMPANY, LIMITED, Chuo-ku (JP)

(*) Notice: Subject to any disclaimer, the term of this patent is extended or adjusted under 35 U.S.C. 154(b) by 936 days.

(21) Appl. No.: 17/766,984

(22) PCT Filed: Aug. 28, 2020

(86) PCT No.: PCT/JP2020/032609
§ 371 (c)(1),
(2) Date: Apr. 6, 2022

(87) PCT Pub. No.: WO2021/070507
PCT Pub. Date: Apr. 15, 2021

(65) Prior Publication Data

US 2023/0022212 A1 Jan. 26, 2023

(30) Foreign Application Priority Data

Oct. 8, 2019 (JP) ................................ 2019-185109

(51) Int. Cl.
*C07H 1/00* (2006.01)
*C07H 11/00* (2006.01)
*C07H 23/00* (2006.01)

(52) U.S. Cl.
CPC ............... *C07H 1/00* (2013.01); *C07H 11/00* (2013.01); *C07H 23/00* (2013.01)

(58) Field of Classification Search
CPC ................................. C07H 1/00; C07H 23/00
USPC .......................................................... 536/4.1
See application file for complete search history.

(56) References Cited

U.S. PATENT DOCUMENTS

| | | | |
|---|---|---|---|
| 8,158,774 | B2 | 4/2012 | Kitagawa et al. |
| 2009/0286970 | A1 | 11/2009 | Kitagawa et al. |
| 2010/0099640 | A1 | 4/2010 | Geuns et al. |
| 2014/0206856 | A1 | 7/2014 | Aoki et al. |
| 2018/0079768 | A1 | 3/2018 | Aoki et al. |
| 2021/0238217 | A1 | 8/2021 | Tanaka et al. |

FOREIGN PATENT DOCUMENTS

| | | | |
|---|---|---|---|
| CN | 101426805 | A | 5/2009 |
| CN | 101522701 | A | 9/2009 |
| CN | 103906758 | A | 7/2014 |
| CN | 107428793 | A | 12/2017 |
| JP | 5168145 | B2 | 3/2013 |
| WO | WO 2008/016079 | A1 | 2/2007 |
| WO | WO 2013/027843 | A1 | 2/2013 |

(Continued)

OTHER PUBLICATIONS

Kobayashi et al., Published Sep. 24, 2019, Chemistry: An Asian Journal, vol. 14, Issue 21, pp. 3921-3937 (Year: 2019).*
International Search Report issued Oct. 20, 2020 in PCT/JP2020/032609 filed Aug. 28, 2020, 2 pages.
English translation of International Preliminary Report on Patentability and Written Opinion issued Apr. 12, 2022 in PCT/JP2020/032609, 4 pages.
Yoshinobu Shiba, et al., "Chemical synthesis of a very long oligoribonucleotide with 2-cyanoethoxymethyl (CEM) as the 2'-O-protecting group: structural identification and biological activity of a synthetic 110mer precursor-microRNA candidate," Nucleic Acids Research, vol. 35, No. 10, 2007, pp. 3287-3296.

(Continued)

*Primary Examiner* — Renee Claytor
*Assistant Examiner* — Jaret J Crews
(74) *Attorney, Agent, or Firm* — Oblon, McClelland, Maier & Neustadt, L.L.P.

(57) ABSTRACT

A purpose of the present invention is to provide a method for producing a glycoside compound having a high purity. The present invention provides a method for producing a glycoside compound represented by formula (3) (wherein $B^a$, i-Pr and n are the same as those defined below), which comprises reacting a glycoside compound of formula (1) (wherein $B^a$ represents an adenine group which may be optionally substituted with an acyl group, and i-Pr represents an isopropyl group) with an ether compound of formula (2) (wherein $R^1$ represents a C1-C6 alkyl group or a phenyl group, and n is 0 or 1) in one or more solvents selected from tetrahydropyran and 4-methyltetrahydropyran in the presence of one or more halogenated agents selected from halogen, N-halogenated succinimide, and N-halogenated hydantoin.

(1)

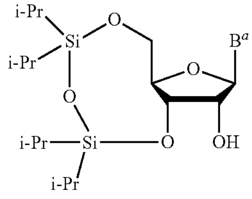

(2)

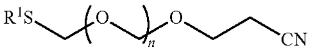

(3)

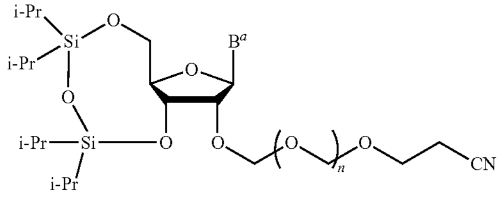

8 Claims, No Drawings

(56) References Cited

FOREIGN PATENT DOCUMENTS

| | | | |
|---|---|---|---|
| WO | WO 2016/159374 | A1 | 10/2016 |
| WO | WO 2019/208571 | A1 | 10/2019 |

OTHER PUBLICATIONS

Extended European Search Report issued Sep. 28, 2023 in European Patent Application No. 20874517.4, 7 pages.

Combined Chinese Office Action and Search Report issued Jun. 11, 2024, in corresponding Chinese Patent Application No. 202080070122.1 (with English Translation), 13 pages.

Xinglong Xing et al., "Synthesis of 1-phenyl-3-(2',3',4',6'-tetra-O-acetyl-β-D-glycopyranosyl)-5-phenyl-2,4-imidazolidinedione", Journal of Suzhou University (Natural Science Edition), vol. 19, No. 02, 2003, 9 pages (with English translation).

* cited by examiner

METHOD FOR PRODUCING GLYCOSIDE COMPOUND

CROSS-REFERENCE TO RELATED APPLICATIONS

The present application is a 35 U.S.C. § 371 national stage patent application of International patent application PCT/JP2020/032609, filed on Aug. 28, 2020, which is based on and claims the benefits of priority to Japanese Application No. 2019-185109, filed on Oct. 8, 2019. The entire contents of these applications are incorporated herein by reference.

TECHNICAL FIELD

This application claims priority to and the benefit of Japanese Patent Application No. 2019-185109 filed Oct. 8, 2019, the entire contents of which are incorporated herein by reference.

RNA, which is a nucleic acid oligomer comprising ribose, can be applied as a RNA probe, an antisense RNA, a ribozyme, a siRNA, or an aptamer and so on, which is a useful material.

BACKGROUND ART

In a method for producing a nucleic acid oligomer, it is used a phosphoramidite compound of nucleoside in which a 3'-position hydroxy group is phosphoramidited. Also as a precursor of phosphoramidite compound of the nucleoside, it is known a glycoside compound in which a 3'-position hydroxy group and a 5'-position hydroxy group of the nucleoside are substituted with a protecting group, and a 2'-position hydroxy group is substituted with a protecting group that is capable of leaving under mild condition.

As a method for producing the glycoside compound, it is known a method for producing a glycoside compound wherein an ether derivative group is introduced into a 2'-position hydroxy group, which comprises a step of reacting a glycoside compound wherein a 3'-position hydroxy group and a 5'-position hydroxy group are protected with a silyl protecting group, with a thioether compound in tetrahydrofuran as a solvent (see Patent Literatures 1 and 2).

CITATION LIST

Patent Literature

Patent Literature 1: JP 5168145 B2
Patent Literature 2: WO 2016/159374

SUMMARY OF THE INVENTION

Problems to be Solved by Invention

The purity of the glycoside compound of the below-mentioned formula (3) which is prepared by the method described in the above-mentioned patent literatures 1 and 2 is not necessarily satisfactory. An object of the present invention is to provide a method for producing a glycoside compound having high purity.

Means to Solve Problems

The present invention provides a method for producing the below-mentioned glycoside compounds. The present invention encompasses aspects described in the below-mentioned Items, but are not limited thereto.

Item [1] A method for producing a glycoside compound represented by formula (3):

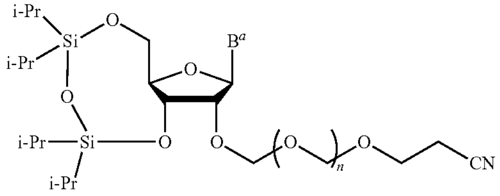

(3)

wherein $B^a$, i-Pr and n are the same as those defined below, which comprises reacting a glycoside compound represented by formula (1):

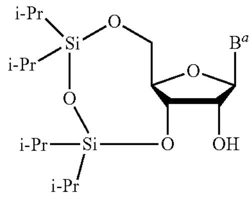

(1)

wherein $B^a$ represents an adenine group which may be optionally substituted with an acyl group, and i-Pr group represents an isopropyl group, with an ether compound represented by formula (2):

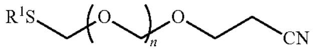

(2)

wherein $R^1$ represents a C1-C6 alkyl group or a phenyl group, and n is 0 or 1, in one or more solvents selected from tetrahydropyran and 4-methyltetrahydropyran in the presence of one or more halogenating agents selected from halogen, N-halogenated succinimide, and N-halogenated hydantoin.

(hereinafter, referred to as "Production Method of present invention" or "Present production method").

Item [2] The method for producing according to [1] wherein n is 1.

Item [3] The method for producing according to [1] wherein n is 0.

Item [4] The method for producing according to any one of [1] to [3] wherein the halogenating agent is halogen.

Item [5] The method for producing according to any one of [1] to [4] wherein the halogenating agent is iodine.

Item [6] The method for producing according to any one of [1] to [5] wherein $R^1$ represents a methyl group.

Item [7] The method for producing according to any one of [1] to [6] wherein $B^a$ represents an adenine group which is substituted with an acetyl group or a benzoyl group.

Item [8] The method for producing according to any one of [1] to [6] wherein $B^a$ represents an adenine group which is substituted with an acetyl group.

Effect of Invention

According to the method for producing of the present invention, a formation of impurities of a glycoside compound which is a starting material for oligonucleic acid synthesis can be suppressed. The glycoside compound is suitable for a synthesis of oligonucleic acid.

MODE FOR CARRYING OUT THE INVENTION

Hereinafter, the present invention is explained in detail.

As used herein, the term "comprise" may encompass also the meanings of "essentially consist of" and "consist of".

A method for producing a glycoside compound represented by formula (3) (hereinafter, referred to as "Process of the present invention" or "Present process") is described herein, said method comprises reacting a glycodide compound represented by formula (1) with an ether compound represented by formula (2) in one or more solvents selected from tetrahydropyran and 4-methyltetrahydropyran in the presence of one or more halogenating agents selected from halogen, N-halogenated succinimide, and N-halogenated hydantoin.

For the glycoside compounds of formula (1) and formula (3), the adenine group which may be optionally substituted with an acyl group indicated as $B^a$ has the following structure.

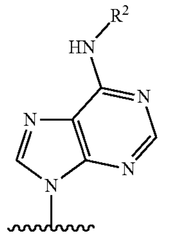

wherein $R^2$ represents a hydrogen atom or an acyl group.

An acyl group represents a straight chain or branched chain of aliphatic acyl group, or an aromatic acyl group, in which the total number of carbon atom including the carbon atom contained in carbonyl group is 2 to 12, and preferably is 2 to 7. Examples of the acyl group include aliphatic acyl groups (such as an acetyl group, a propionyl group, a butanoyl group (a butyryl group), an isobutanoyl group (an isobutyryl group), a pentanoyl group, a hexanoyl group, a heptanoyl group, an octanoyl group, a nonanoyl group, a decanoyl group, and an undecanoyl group, and so on); and an aromatic acyl groups (such as a benzoyl group, a 1-naphtoyl group, and a 2-naphtoyl group), and preferably include an acetyl group or a benzoyl group.

Examples of the halogenated agent include halogens (such as iodine and bromine); N-halogenated succinimides (such as N-chloro succinimide, N-bromo succinimide (NBS), and N-iodo succinimide (NIS) and so on); N-halogenated hydantoins (such as 1,3-diiodo-5,5-dimethyl hydantoin, 1,3-dibromo-5,5-dimethyl hydantoin, and 1-bromo-3-chloro-5,5-dimethyl hydantoin, and so on). In the present invention, halogens are preferably used, and iodine is further preferably used.

The reaction of the present invention may be conducted by adding an acid in addition to the halogenated agents. Examples of the acid include perfluoroalkyl carboxylic acids and salts thereof, alkyl sulfonic acids and salts thereof, aryl sulfonic acids and salts thereof, perfluoroalkyl sulfonic acid and its salt, and alkyl sulfonic acids and salts thereof, as well as any combinations of two or more of these acids. Examples of the salt include metal salts (such as copper salt and silver salt). Specific examples of the acid include methanesulfonic acid, p-toluenesulfonic acid, camphor sulfonic acid, trifluoromethanesulfonic acid, and silver trifluoromethanesulfonate, as well as any combinations of two or more of these acids. The alkyl group of alkylsulfonic acid may be a straight chain or branched chain thereof, and preferably is an alkyl group having 1 to 6 of carbon atoms. As an example of the alkyl group, methyl, ethyl, n-propyl, isopropyl, n-butyl, isobutyl, tert-butyl, n-pentyl, isopentyl, and hexyl are exemplified. Examples of the aryl group of aryl sulfonic acid include phenyl group and tolyl group.

For the ether compound of formula (2), the alkyl group indicated as $R^1$ may be a straight chain or branched chain thereof, and preferably is an alkyl group having 1 to 6 of carbon atoms. Examples of the alkyl group include methyl, ethyl, n-propyl, isopropyl, n-butyl, isobutyl, tert-butyl, n-pentyl, isopentyl, and hexyl. Examples of the alkyl group include preferably a methyl group.

Examples of the solvent for the reaction of the present invention include tetrahydropyran compounds, and specific examples thereof include tetrahydropyran (THP) and 4-methyltetrahydropyran (MTHP), and mixed solvents of these solvents. The amount of solvent is within a range of usually 0.5 v/w to 20 v/w %, and preferably 1 v/w to 10 v/w %, as opposed to the glycoside compound represented by formula (1).

The amount of the ether compound represented by formula (2) is within a range of usually 0.8 to 5 moles, preferably 1 to 3 mole(s), and more preferably 1 to 1.5 mole(s), as opposed to 1 mole of the glycoside compound represented by formula (1). The amount of the halogenated agents is within a range of usually 0.8 to 10 moles, preferably 3 to 10 moles, and more preferably 3 to 6 moles, as opposed to 1 mole of the glycoside compound represented by formula (1). The amount of the acid is within a range of usually 0 to 5 moles, preferably 0 to 1.5 moles, and more preferably 0 to 0.1 moles, as opposed to 1 mole of the glycoside compounds represented by formula (1).

The reaction temperature of the present invention is usually within a range of −30 to 30° C., preferably −20 to 25° C., and more preferably −15 to 5° C. The reaction period of the present reaction is within a range of usually 0.5 to 10 hours, and preferably 0.5 to 6 hours.

The glycoside compound represented by formula (1) can be prepared by a publicly known method, or can be obtained as a commercially available product. The ether compound represented by formula (2) can be prepared according to a publicly known method (see the above-mentioned patent literatures 1, 2 and JP 2016-50203 A).

The glycoside compound obtained by the present invention may be used as a crude product in a next reaction, and as needed, may be purified by a silica gel column chromatography.

EXAMPLES

Hereinafter, working examples are described to explain the present invention in more detail. The present invention, however, is not limited to these examples and so on.

The purity of the synthesized glycoside compound was measured by HPLC. The glycoside compound was separated to each ingredient by HPLC, and for the amount of by-products, the total of area percentages of the by-products in the obtained chromatograms were calculated. The used HPLC apparatus was set such that any peaks having peak area of 1,000 or more can be detected, and the peak having minimum peak area which was detectable under this condition was 0.03% as area percentage.

TABLE 1

| | |
|---|---|
| Column | XBridge BEH C18 XP Column. 130 Å, 2.5 μm, 3 mm x 50 mm (Waters) |
| Flow rate | 1.0 mL/min |
| Detection wavelength | 260 nm |
| Mobile phase A | 10 mM TEAA (triethylamine acetate buffer), pH 7.0 |
| Mobile phase B | Acetonitrile |
| Gradient | B conc. 5%-75% |
| Column temperature | 35° C. |

Hereinafter, as used herein, CEM represents 2-cyanoethoxymethyl, and EMM represents 2-cyanoethoxymethoxymethyl.

Example 1

$N^6$-Acetyl-3',5'-O-(tetraisopropyldisiloxan-1,3-diyl)-2'-O-(2-cyanoethoxymethoxymethyl)adenosine (EMM A)

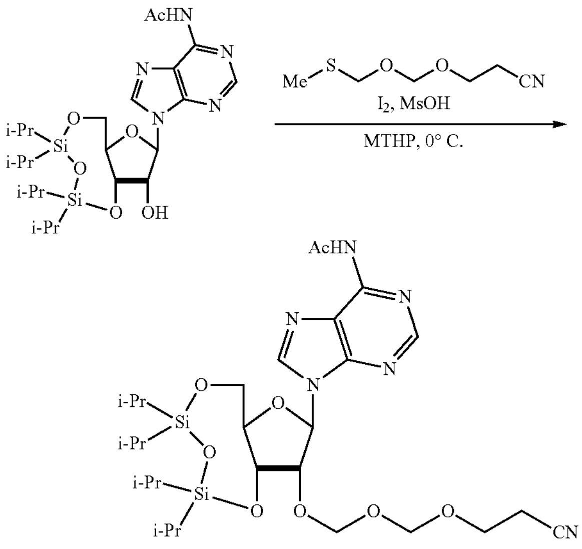

EMM A $N^6$-Acetyl-3',5'-O-(tetraisopropyldisiloxan-1,3-diyl)adenosine (1.0 g, 1.8 mmol) was dissolved in 4-methyltetrahydropyran (10 mL), and the mixture was cooled to 0° C. Thereto were added methanesulfonic acid (17 mg, 0.18 mmol), iodine (2.7 g, 10.8 mmol), and 2-cyanoethoxymethyl methylthiomethyl ether (0.44 g, 2.7 mmol), and the mixture was stirred at 0° C. under nitrogen atmosphere for 3 hours. The reaction solutions were added to a mixed solution of saturated aqueous sodium thiosulfate solution and saturated aqueous sodium hydrocarbonate solution, and the mixture was extracted with ethyl acetate. The solvents were evaporated to obtain a crude product containing a desired product.

As a result of HPLC analysis, the total of LC peak area of the by-products was 5.9%.

Example 2

$N^6$-Acetyl-3',5'-O-(tetraisopropyldisiloxan-1,3-diyl)-2'-O-(2-cyanoethoxymethyl)adenosine (CEM A)

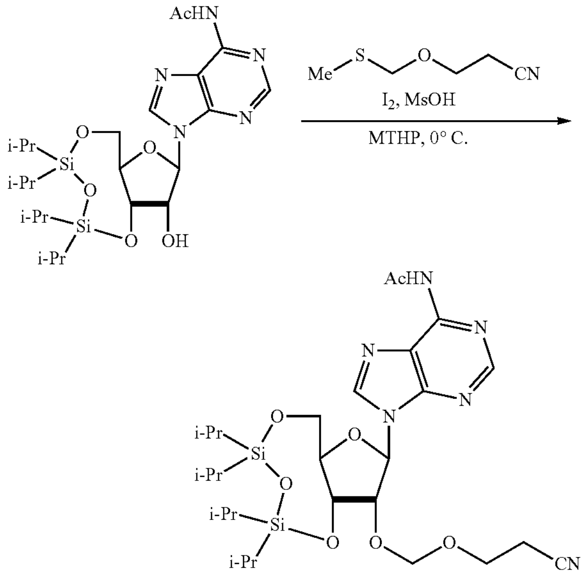

CEM A $N^6$-Acetyl-3',5'-O-(tetraisopropyldisiloxan-1,3-diyl)adenosine (1.0 g, 1.8 mmol) was dissolved in 4-methyltetrahydropyran (5 mL), and the mixture was cooled to 0° C. Thereto were added methanesulfonic acid (17 mg, 0.18 mmol), iodine (2.7 g, 10.8 mmol), and methylthiomethyl 2-cyanoethyl ether (0.35 g, 2.7 mmol), and the mixture was stirred at 0° C. under nitrogen atmosphere for 3 hours. The reaction solutions were added to a mixed solution of saturated aqueous sodium thiosulfate solution and saturated aqueous sodium hydrocarbonate solution, and the mixture was extracted with ethyl acetate. The solvents were evaporated to obtain a crude product containing a desired product.

As a result of HPLC analysis, the total of LC peak area of the by-products was 3.3%.

Examples 3

$N^6$-Acetyl-3',5'-O-(tetraisopropyldisiloxan-1,3-diyl)-2'-O-(2-cyanoethoxymethoxymethyl)adenosine (EMM A)

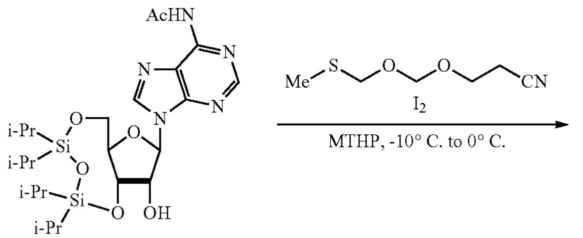

-continued

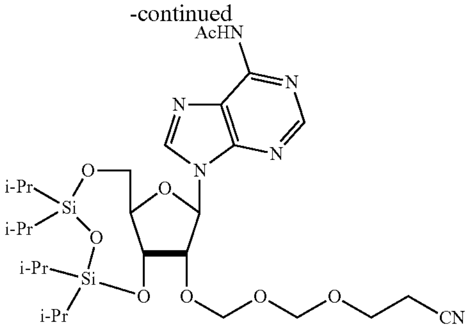

EMM A $N^6$-Acetyl-3',5'-O-(tetraisopropyldisiloxan-1,3-diyl)adenosine (5.0 g, 9.0 mmol) was dissolved in toluene (25 mL), and the mixture was concentrated to 15 mL as a solution volume. To this solution was added 4-methyltetrahydropyran (10 mL), and the mixture was cooled to −10° C. Thereto were added iodine (13.8 g, 55.2 mmol), and 2-cyanoethoxymethyl methylthiomethyl ether (2.18 g, 13.4 mmol), and the mixture was stirred at 0° C. under nitrogen atmosphere for 1 hour. The reaction solution was added to a mixed solution of saturated aqueous sodium thiosulfate solution and saturated aqueous sodium hydrocarbonate solution, and the mixture was extracted with toluene. The solvents were evaporated to obtain a crude product containing a desired product.

As a result of HPLC analysis, the total of LC peak area of the by-products was 7.1%.

Comparative Example 1

$N^6$-Acetyl-3',5'-O-(tetraisopropyldisiloxan-1,3-diyl)-2'-O-(2-cyanoethoxymethoxymethyl)adenosine (EMM A)

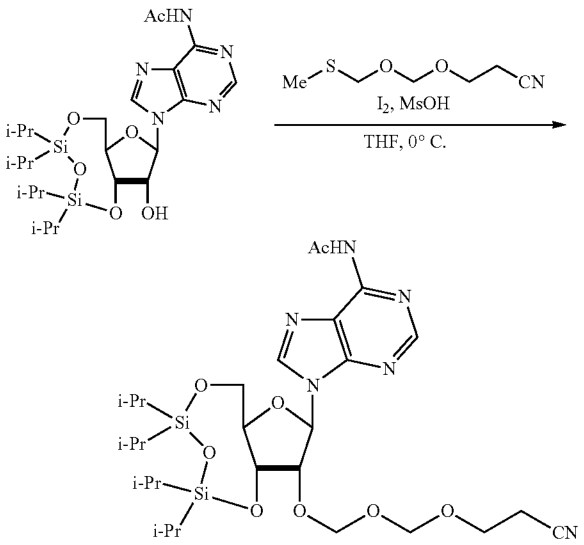

EMM A $N^6$-Acetyl-3',5'-O-(tetraisopropyldisiloxan-1,3-diyl)adenosine (1.0 g, 1.8 mmol) was dissolved in tetrahydrofuran (10 mL), and the mixture was cooled to 0° C. Thereto were added methanesulfonic acid (17 mg, 0.18 mmol), iodine (2.7 g, 10.8 mmol), and 2-cyanoethoxymethyl methylthiomethyl ether (0.44 g, 2.7 mmol), and the mixture was stirred at 0° C. under nitrogen atmosphere for 3 hours. The reaction solution was added to a mixed solution of saturated aqueous sodium thiosulfate solution and saturated aqueous sodium hydrocarbonate solution, and the mixture was extracted with ethyl acetate. The solvents were evaporated to obtain a crude product containing a desired product.

As a result of HPLC analysis, the total of LC peak area of the by-products was 10.2%.

Comparative Example 2

$N^6$-Acetyl-3',5'-O-(tetraisopropyldisiloxan-1,3-diyl)-2'-O-(2-cyanoethoxymethyl)adenosine (CEM A)

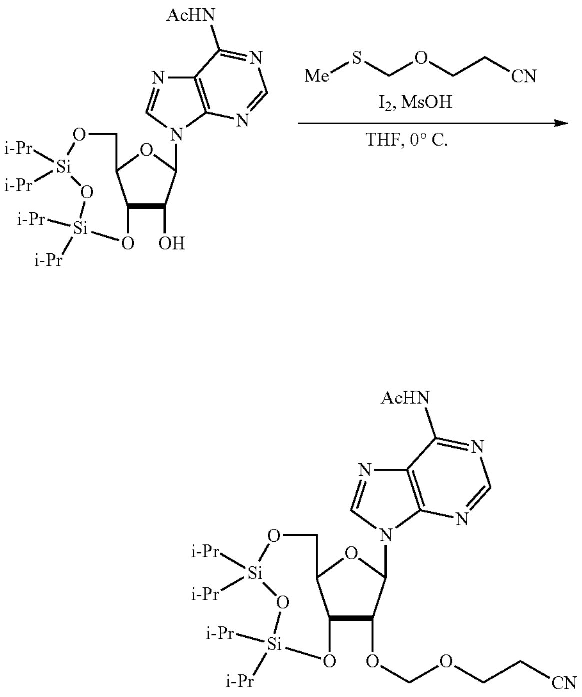

CEM A $N^6$-Acetyl-3',5'-O-(tetraisopropyldisiloxan-1,3-diyl)adenosine (1.0 g, 1.8 mmol) was dissolved in tetrahydrofuran (5 mL), and the mixture was cooled to 0° C. Thereto were added methanesulfonic acid (17 mg, 0.18 mmol), iodine (2.7 g, 10.8 mmol), and methylthiomethyl 2-cyanoethyl ether (0.35 g, 2.7 mmol), and the mixture was stirred at 0° C. under nitrogen atmosphere for 3 hours. The reaction solutions were added to a mixed solution of saturated aqueous sodium thiosulfate solution and saturated aqueous sodium hydrocarbonate solution, and the mixture was extracted with ethyl acetate. The solvents were evaporated to obtain a crude product containing a desired product.

As a result of HPLC analysis, the total of LC peak area of the by-products was 8.6%.

Comparative Example 3

$N^6$-Acetyl-3',5'-O-(tetraisopropyldisiloxan-1,3-diyl)-2'-O-(2-cyanoethoxymethoxymethyl)adenosine (EMM A)

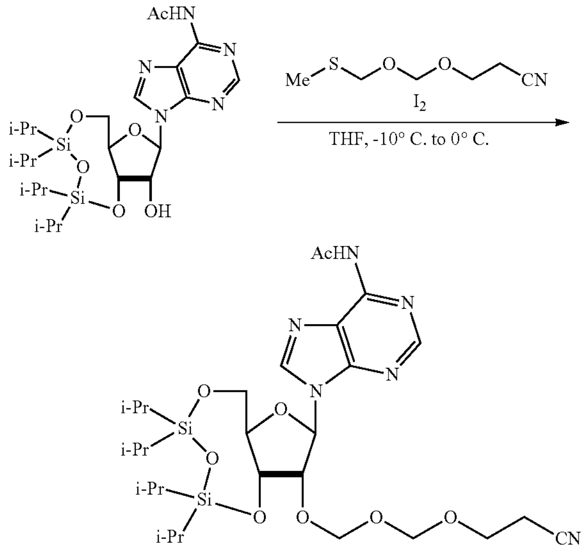

EMM A $N^6$-Acetyl-3',5'-O-(tetraisopropyldisiloxan-1,3-diyl)adenosine (5.0 g, 9.0 mmol) was dissolved in toluene (25 mL), and the mixture was concentrated to 15 mL as a solution volume. To this solution was added tetrahydrofuran (10 mL), and the mixture was cooled to −10° C. Thereto were added iodine (13.8 g, 55.2 mmol) and 2-cyanoethoxymethyl methylthiomethyl ether (2.18 g, 13.4 mmol), and the mixture was stirred at 0° C. under nitrogen atmosphere for 1 hour. The reaction solution was added to a mixed solution of saturated aqueous sodium thiosulfate solution and saturated aqueous sodium hydrocarbonate solution, and the mixture was extracted with toluene. The solvents were evaporated to obtain a crude product containing a desired product.

As a result of HPLC analysis, the total of LC peak area of the by-products was 10.7%.

Test results of the above-mentioned Examples and Comparative Examples are shown in Table 2.

TABLE 2

| Desired product | Solvent | Acid | Amount of By-product (HPLC) | Total number of peaks of by-products (HPLC) |
|---|---|---|---|---|
| EMM A | MTHP | Added | 5.9% (Example 1) | 27 |
| | THF | Added | 10.2% (Comparative Example 1) | 39 |
| | MTHP | Non-added | 7.1% (Example 3) | 19 |
| | THF | Non-added | 10.7% (Comparative Example 3) | 33 |

TABLE 2-continued

| Desired product | Solvent | Acid | Amount of By-product (HPLC) | Total number of peaks of by-products (HPLC) |
|---|---|---|---|---|
| CEM A | MTHP | Added | 3.3% (Example 2) | 15 |
| | THF | Added | 8.6% (Comparative Example 2) | 27 |

As shown in Table 2 above, using 4-methyltetrahydropyran (MTHP) as a solvent can suppress a formation of the by-products, which can obtain the desired product in higher purity.

INDUSTRIAL APPLICABILITY

According to the present invention, a method for producing a glycoside compound is provided. The glycoside compound that is obtained according to the process has a high purity, and is suitable for synthesis of oligonucleotide with high purity.

The invention claimed is:

1. A method for producing a glycoside compound represented by formula (3):

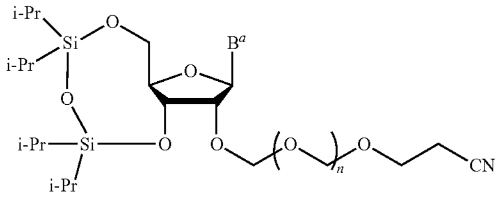

(3)

where $B^a$ represents an adenine group which may be optionally substituted with an acyl group, i-Pr group represents an isopropyl group, and n is 0 or 1, the method comprising:

reacting a glycoside compound represented by formula (1):

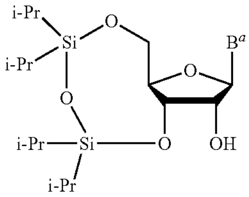

(1)

wherein $B^a$ represents an adenine group which may be optionally substituted with an acyl group, and i-Pr group represents an isopropyl group, with an ether compound represented by formula (2):

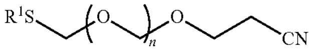

(2)

wherein $R^1$ represents a C1-C6 alkyl group or a phenyl group, and n is 0 or 1, in 4-methyltetrahydropyran in the presence of at least one halogenating agent selected from the group consisting of halogen, N-halogenated succinimide, and N-halogenated hydantoin.

2. The method for producing according to claim 1 wherein, in the formulas (2) and (3), n is 1.

3. The method for producing according to claim 1 wherein, in the formulas (2) and (3), n is 0.

4. The method for producing according to claim 1 wherein the halogenating agent is halogen.

5. The method for producing according to claim 1 wherein the halogenating agent is iodine.

6. The method for producing according to claim 1 wherein $R^1$ represents a methyl group.

7. The method for producing according to claim 1 wherein, in the formulas (1) and (3), $B^a$ represents an adenine group which is substituted with an acetyl group or a benzoyl group.

8. The method for producing according to claim 1 wherein, in the formulas (1) and (3), $B^a$ represents an adenine group which is substituted with an acetyl group.

* * * * *